United States Patent [19]

Horton et al.

[11] 4,024,333
[45] May 17, 1977

[54] SYNTHESIS OF DAUNOSAMINE HYDROCHLORIDE FROM A D-MANNOSE STARTING MATERIAL

[75] Inventors: Derek Horton; Wolfgang F. Weckerle, both of Columbus, Ohio

[73] Assignee: The United States of America as represented by the Department of Health, Education and Welfare, Washington, D.C.

[22] Filed: June 22, 1976

[21] Appl. No.: 698,689

[52] U.S. Cl. .................................. 536/17; 536/4; 536/18; 424/180

[51] Int. Cl.[2] ...................................... C07G 11/00

[58] Field of Search ............................. 536/18, 17

[56] References Cited

OTHER PUBLICATIONS

Evans, Carbohydrate Research, vol. 21, (1972) pp. 473–475.
Beynon et al., J. Chem. Soc. (c), 1969, pp. 272–281.
Acton et al., "Commun. to the Editor," J. of Med. Chem., 1974, vol. 17, No. 6, pp. 659–660.
Gaylord, "OXIMES," Red. w/Complex Metal Hydrides, p. 751, Intersci. Publ. NY 1956.

*Primary Examiner*—Lewis Gotts
*Assistant Examiner*—Cary Owens

[57] ABSTRACT

A method for synthesizing daunosamine hydrochloride from methyl α-D-mannopyranoside. The major features of the preparative route involve the formation of a 2-deoxy-3-keto intermediate, whose oxime is reduced with high stereoselectivity to the D-ribo-3-amino compound, followed by a stereospecific step late in the sequence to introduce the terminal C-methyl group with inversion at C-5, to generate the required L-lyxo stereochemistry. The synthesis procedure affords daunosamine hydrochloride in 40% overall yield, with no chromatographic procedures for isolation being required in any of the steps.

5 Claims, No Drawings

SYNTHESIS OF DAUNOSAMINE HYDROCHLORIDE FROM A D-MANNOSE STARTING MATERIAL

BACKGROUND OF THE INVENTION

This invention relates to the production of daunosamine and, more particularly, to a novel synthetic route for the preparation of daunosamine hydrochloride from a D-mannose starting material.

The anthracycline antibiotics daunorubicin (daunomycin) and adriamycin, particularly the latter, have shown considerable promise as anticancer agents in clinical use. In view of the high cost of microbially producing these antibiotics, various attempts have recently been made to develop an effective synthetic route for their production. One approach, proposed by Acton et al., J. Med. Chem., 17 (1974) 659–660, involves a coupling reaction between the separately prepared amino sugar and aglycone constituents of the antibiotic.

Daunosamine (3-amino-2,3,6-trideoxy-L-lyxo-hexose) is the amino sugar constituent of both daunorubicin and adriamycin. A synthesis of daunosamine isolated as its hydrochloride by a route starting from L-rhamnose (6-deoxy-L-mannose) has been proposed by Marsh et al., Chem. Commun., (1967) 973–975. The Marsh et al., procedure, however, suffers from several drawbacks. First of all, L-rhamnose is a relatively expensive starting sugar for the preparation of daunosamine. Secondly, the route described by Marsh et al., requires several steps involving chromatographic resolution, and gives daunosamine in relatively low overall yield.

SUMMARY OF THE INVENTION

It is, accordingly, a primary object of this invention to provide a convenient method for synthesizing daunosamine from a relatively abundant and inexpensive sugar precursor.

Another object of this invention is to provide a method of synthesis in accordance with the preceding object, which provides a relatively high overall yield of daunosamine.

A further object of this invention is to provide a method of synthesis in accordance with the preceding objects, which requires no chromatographic procedures for isolation in any of the steps thereof.

Still another object of this invention is to provide a method of synthesis in accordance with the preceding objects, from a D-mannose starting material.

The above and other objects are achieved in accordance with the present invention by providing a method for the synthesis of daunosamine isolated as its hydrochloride from a D-mannose starting material consisting of methyl α-D-mannopyranoside. In general terms, the method is characterized by conversion of the D-mannose starting material into a 2-deoxy-3-keto intermediate whose oxime is reduced with high stereoselectivity to introduce the correctly oriented D-ribo-3-amino group, followed by a stereospecific step late in the sequence to introduce the terminal C-methyl group with inversion at C-5, to generate the required L-lyxo stereochemistry. The method results in the production of daunosamine hydrochloride in 40% overall yield, without any chromatographic procedures for isolation being required in any of the steps.

More specifically, the steps of the method are described below with reference to the following schematic diagram of the synthesis procedure, wherein Me is methyl, Ph is phenyl, Bu is butyl, Ac is acetyl, and Bz is benzoyl.

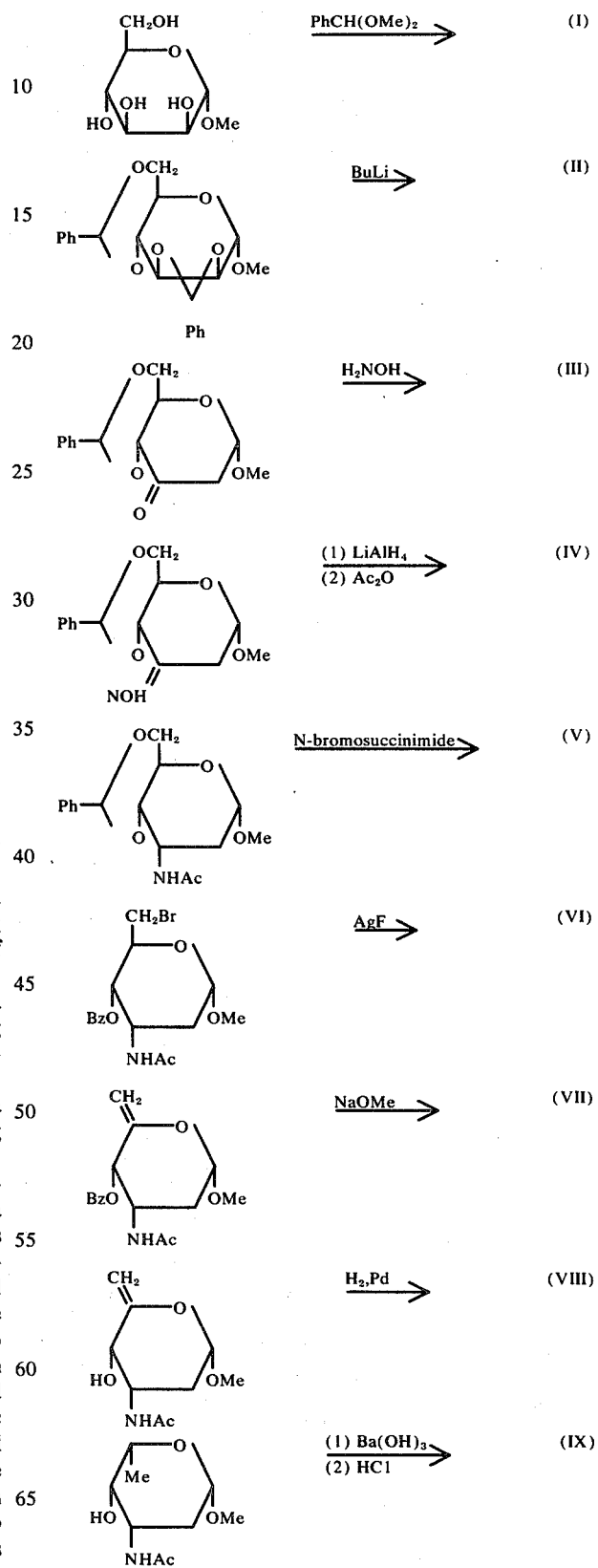

-continued

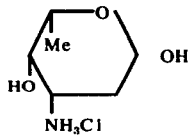
(X)

As illustrated in the above schematic diagram, the D-mannose starting material, methyl α-D-mannopyranoside (Compound I), is first benzylidenated with α,α-dimethoxytoluene to the 2,3,:4,6-dibenzylidene acetal (Compound II), which is then converted with butyllithium into the 4,6-O-benzylidene-2-deoxy-3-keto compound (Compound III). The 3-keto group is then oximated with hydroxylamine to the 3-oxime group (resulting in Compound IV), which is then reduced with lithium aluminum hydride to the 3-amino group which, in turn, is acetylated with acetic anhydride to the 3-acetamido group. From the resulting reaction mixture of D-ribo and D-arabino diastereoisomers, the 4,6-O-benzylidene-ribo-3-acetamido compound (Compound V) is recovered and then converted with N-bromosuccinimide into the 4-O-benzoyl-6-bromo-6-deoxy compound (Compound VI). Compound VI is then dehydrobrominated with silver fluoride to the 5,6-unsaturated compound (Compound VII), which is then debenzoylated by catalytic transesterification with sodium methoxide to the 4-hydroxy-5,6-unsaturated compound (Compound VIII). Compound VIII is then stereospecifically hydrogenated in the presence of palladium-on-barium sulfate to give methyl N-acetyl-β-daunosaminide (Compound IX), which is then N-deacylated with aqueous barium hydroxide and hydrolyzed with aqueous hydrochloric acid to give daunosamine hydrochloride (Compound X).

DESCRIPTION OF PREFERRED EMBODIMENTS

The methyl α-D-mannopyranoside employed as a starting material in the synthesis procedure in accordance with the present invention, is a known compound which may either be obtained commercially, for example, from Pfannstiehl Chemical Co., Waukegan, Ill., or prepared in known manner by methylation of the naturally occurring and abundant D-mannose.

Benzylidenation of the methyl α-D-mannopyranoside to Compound II with α,α-dimethoxytoluene is carried out by the general procedure described by Evans, Carbohydr. Res., 21 (1972) 473–475. The reaction is carried out at temperatures within the range of from 60°–75° C for 1 to 5 hours, preferably 3 hours, in an aprotic dipolar solvent, such as N,N-dimethylformamide, in the presence of an acidic catalyst, such as anhydrous p-toluenesulfonic acid. The molar ratio of α,α-dimethoxytoluene to methyl α-D-mannopyranoside should be at least 2:1, preferably about 2.3:1. Compound II may be recovered in 95% yield as a crystalline mixture of products diastereoisomeric at the acetal position of the dioxolane ring, by pouring the reaction mixture with vigorous stirring into ice water containing sodium hydrogen carbonate and filtering and drying the resultant precipitate. Purification to give a single diastereoisomer is not necessary for the next step in the sequence.

Conversion of Compound II into the key intermediate Compound III with butyllithium is carried out at temperatures below −30° C, preferably within the range of from −30° to −55° C, for a period of time ranging from 0.5 to 2 hours in a tetrahydrofuran solvent. The molar ratio of butyllithium to Compound II should be at least 2:1, preferably about 2.2:1. The butyllithium reagent appears to attack the dioxolane ring of Compound II specifically, with abstraction of the axially attached hydrogen atom (H-3) to generate the enolate anion of Compound III with release of benzaldehyde (which reacts with a second molecule of the reagent). Both of the dioxolane-ring isomers of Compound II react to give the same product, but the reagent does not attack the 1,3-dioxane ring of Compound II. Compound III may be isolated crystalline in 91% yield by pouring the reaction mixture with vigorous stirring into ice water containing ammonium chloride, evaporating off the tetrahydrofuran solvent, cooling the aqueous slurry to 0° C, and filtering and drying the crystalline Compound III.

Oximation of Compound III to Compound IV with hydroxylamine is carried out by the procedure described by Beynon et al., J. Chem. Soc., C, (1969) 272–281. This procedure involves adding Compound III to a solution of hydroxylamine in ethanol at room temperature, employing a large molar excess, preferably about five-fold, of hydroxylamine to Compound III. After about 30 minutes, Compound IV will begin to precipitate. The solution is then cooled to a temperature within the range of from −10° to +5° C, preferably about 0° C, and maintained thereat for at least 10 to 12 hours. The precipitate is then separated from the reaction mixture by filtration to provide Compound IV in greater than 95% yield.

Reduction of the 3-oxime group of Compound IV to the 3-amino group with lithium aluminum hydride is carried out in an ether or tetrahydrofuran solvent under reflux for a period of from 24 to 48 hours. The molar ratio of lithium aluminum hydride to Compound IV is at least 2:1 up to about 5:1, preferably about 3.75:1. The resultant product is then acetylated directly with acetic anhydride to convert the 3-amino group to the 3-acetamido group. The acetylation is carried out at room temperature for a period of from 12 to 24 hours, preferably about 18 hours, in a pyridine solvent. The molar ratio of acetic anhydride to the 3-amino compound is within the range of from 3:1 to 10:1, preferably about 5:1, and the volume ratio of the pyridine solvent to acetic anhydride is preferably within the range of from 1.5:1 to about 2:1. The resultant reaction products are a mixture containing 87% of the D-ribo Compound V and 12% of the corresponding D-arabino diastereoisomer. These two products are readily separated, without recourse to chromatography, by exploiting the very low solubility of the D-arabino diastereoisomer in toluene. Mixing of the reaction mixture with toluene at a temperature within the range of from 0° C to room temperature, preferably at about 0° C, for about 15 minutes to 1 hour, results in the precipitation of the arabino-3-acetamido compound. The precipitate is then filtered off, and the mother liquor evaporated to provide the desired ribo Compound V in 87% yield.

The reaction of Compound V with N-bromosuccinimide is carried out in a dry carbon tetrachloride solvent under reflux for a period of about one to three hours, preferably about two hours. The molar ratio of N-bromosuccinimide to Compound V should be within the range of from 1:1 to 1.2:1. This reaction leads to opening of the 1,3-dioxane ring and formation of Compound VI, which is isolated crystalline in 70% yield by removing the solvent in vacuo, extracting the residue with dichloromethane, washing the clear extract successively with 5% aqueous sodium hydrogen sulfite and aqueous sodium hydrogen carbonate, drying, evaporating, and recrystallizing from ethanol.

Dehydrobromination of Compound VI with silver fluoride is carried out by the established general procedure in a dry pyridine solvent at room temperature for about eight to twenty hours, preferably about fourteen hours. The weight ratio of silver fluoride to Compound VI is within the range of from 0.8:1 to 1.5:1, preferably about 1:1. The 5,6-unsaturated Compound VII is recovered in quantitative yield by pouring the reaction mixture into ether, filtering, evaporating the filtrate, adding toluene to and evaporating it from the residue to remove all of the pyridine solvent, taking the resultant syrup up in ether, filtering the suspension through a silica gel column to remove residual silver salts, and evaporating the effluent in vacuo.

Debenzoylation of Compound VII by catalytic transesterification is carried out at room temperature for 8 to 20 hours, preferably about 12 hours, in the presence of a catalytic amount of sodium methoxide. The sodium methoxide is employed in the form of a 0.01 to 0.1, preferably about 0.02, molar solution in methanol, with 5 to 6 ml of such solution being employed per gram of Compound VII. The reaction mixture is then passed through a silica gel column, and the effluent evaporated in vacuo to give Compound VIII in 97% yield.

Hydrogenation of Compound VIII is carried out at room temperature and atmospheric pressure for 0.5 to 1 hour in a methanol or ethanol solvent in the presence of 1 to 10% of a palladium-on-barium sulfate catalyst. The reaction is fully stereospecific with net C-5 inversion to give Compound IX in essentially quantitative yield, with none of the 5-epimer being present in the product. Compound IX is recovered from the reaction mixture by filtering off the catalyst and evaporating the filtrate in vacuo.

N-deacylation of Compound IX with aqueous barium hydroxide is carried out under reflux for 10 to 24 hours, preferably 12 hours. The molar ratio of barium hydroxide to Compound IX is from 2:1 to 5:1. The N-deacylated compound is then hydrolyzed with aqueous hydrochloric acid at a temperature of from 60°–100° C for at least one half hour, and preferably about 3 hours, to give the final daunosamine hydrochloride (Compound X) in 84% yield. The net yield of daunosamine hydrochloride from the methanol α-D-mannopyranoside starting material (Compound I) is 40%, based on intermediates isolated directly and without recourse to chromatographic purification at any of the stages.

The daunosamine hydrochloride prepared by the above-described synthesis procedure in accordance with the present invention, can be utilized in the synthetic production of the anthracycline antibiotics daunorubicin and adriamycin, for example, by the coupling procedure described by Acton et al., J. Med. Chem., 17 (1974) 659–660. Thus, the daunosamine moiety may be coupled to daunomycinone, the aglycone of daunorubicin, by the Acton et al procedure to produce daunorubicin, which in turn, can be readily converted to adriamycin by known methods, for example, by the method described by Arcamone et al., Chim. Ind. (Milan), 51, 834 (1969).

The invention is further illustrated by way of the following examples.

EXAMPLE 1

Preparation of methyl 2,3:4,6-di-O-benzylidene-α-D-mannopyranoside (Compound II)

A mixture of methyl α-D-mannopyranoside (Compound I, 50 g, 258 mmoles), α,α-dimethoxytoluene (92 g, 600 mmoles), and anhydrous p-toluene-sulfonic acid (1 g) in N,N-dimethylformamide (300 ml), in a 1-liter flask fitted with an air condenser attached to a water aspirator, was stirred magnetically and heated in an oil bath for 3 hours at 65°–75° C. None of the starting Compound I remained after this time (t.l.c., 4:1 ether-petroleum ether). The mixture was poured with vigorous stirring into 1 liter of ice-water containing sodium hydrogen carbonate (30 g). The resultant precipitate was filtered off, resuspended in ice-water, filtered off again, and dried in air and finally in vacuo over phosphorus pentaoxide; yield 90.6 g (95%), m.p. 120°–160° C, $[\alpha]_D^{23}$ −33° (c 1, chloroform).

Anal. Calc. for $C_{12}H_{22}O_6$ (370.41):C, 68.10; H, 5.99. Found: C, 68.06; H, 6.04.

The product, sufficiently pure for the following step of Example 2, appeared from its n.m.r. spectrum to be a diastereoisomeric mixture at the carbon atom of the 2,3-acetal.

EXAMPLE 2

Conversion to methyl 4,6-O-benzylidene-2-deoxy-α-D-erythrohexopyranosid-3-ulose (Compound III)

A solution of the diastereoisomeric mixture of acetals from the preceding preparation (Compound II, 20 g, 54 mmoles) in commercial absolute tetrahydrofuran (400 ml) under nitrogen was cooled to −40° C. Butyllithium in hexane (2.4M, 50 ml, 120 mmoles) was added, and the temperature was kept for 0.5 hour below −30° C, during which time the color of the solution turned from yellow to red and all of the starting material disappeared, as indicated by t.l.c. monitoring. T.l.c. plates were developed with 1:1 ether-petroleum ether, and the developed plates were heated in vacuo for 15 minutes at 125° C before being sprayed with sulfuric acid for zone detection. The heating step was required for removal of 1-phenyl-1-pentanol, whose $R_f$ value is the same as that of Compound II. The solution, still at −30° C or below, was then poured with vigorous mechanical stirring into ice-water (400 ml) containing ammonium chloride (50 g). Without separation of the layers, the tetrahydrofuran was removed on a rotary evaporator at a bath temperature of 30° C. The aqueous slurry remaining was cooled to 0° C, and the crystalline deoxy ketone (Compound III) was filtered off with use of suction and dried; yield 13 g (49 mmoles, 91%). This product could be used without further purification for the following oximation step of Example 3.

Recrystallization from ethanol gave pure Compound III, m.p. 170°–171° C, $[\alpha]_D^{22}$ +150° (c 1, ethyl acetate); $\nu_{max}^{KBr}$ 1740 (C=O), 745 and 695 cm$^{-1}$ (aryl); X-ray powder diffraction data: 13.18 vw, 9.71 m, 8.58 m, 7.56 vw, 6.83 m, 5.66 m, 5.26 w, 4.86 vw, 4.51 w, 4.18 s (2), 3.77 vs (1), and 3.46 m (3).

The product was indistinguishable from an authentic sample (by i.r., n.m.r., and mass spectrometry).

EXAMPLE 3

Oximation to methyl 4,6-O-benzylidene-2-deoxy-α-D-erythrohexopyranosid-3-ulose oxime (Compound IV)

The deoxy ketone (Compound III, 25 g, 94.7 mmoles) was added to a solution of hydroxylamine (about 500 mmoles) in ethanol at 25° C. After 30 minutes, the oxime (Compound IV) began to precipitate. The solution was then cooled to 0° C and maintained thereat overnight. The oxime product was then separated from the solution by filtration. Yield 26 g (98.5%), m.p. 208° C (from ethanol), $[\alpha]_D^{23}$ +202° (c 1.2, chloroform) $\nu_{max}^{KBr}$ 3330 (OH), 1670 (C=N), 750 and 695 cm$^{-1}$ (aryl); X-ray powder diffraction data: 8.84 w, 8.22 m, 6.70 s (3,3), 5.69 m, 5.29 s (3,3), 4.50 m, 4.11 vs (1), 3.70 s (2), 3.20 vw, and 3.15 m.

EXAMPLE 4

Conversion to methyl 3-acetamido-4,6-O-benzylidene-2,3-dideoxy-α-D-ribo-hexopyranoside (Compound V)

In a 2-liter flask equipped with a magnetic stirrer, a Soxhlet extractor, and a reflux condenser was placed lithium aluminum hydride (12 g, 316 mmoles) in ether (1 liter); and in the extractor thimble was placed the oxime (Compound IV, 23.5 g, 84.3 mmoles). The contents of the flask were stirred and heated under reflux for 24 hours, after which time the excess of the reducing agent was decomposed by successively adding water (12 ml), 15% aqueous sodium hydroxide (12 ml), and water (36 ml). The resultant mixture was filtered, and the filtrate evaporated to give a crystalline residue; this was dissolved in pyridine (140 ml), and acetic anhydride (70 ml) was added, with cooling to 0° C. After 18 hours at 25° C, the solution was poured into ice-water (600 ml), and the product extracted with dichloromethane (3 × 100 ml). The extract was successively washed with aqueous sodium hydrogen carbonate and water, dried (magnesium sulfate), and evaporated in vacuo. Pyridine (two 50-ml portions) and toluene (two 50-ml portions) were successively added to and evaporated from the residue. To the semicrystalline residue resulting was added toluene (120 ml), and the mixture was cooled to 0° C. The crystalline precipitate was then filtered off with suction, and washed with a small volume of cold toluene, to afford the arabino analogue of Compound V; yield 3.2 g (12.3%). Recrystallization from acetone gave long needles, m.p. 272° C (sublimation), $[\alpha]_D^{23}$ +68° (c 0.7, chloroform) $\nu_{max}^{KBr}$ 3270 (NH), 1650, 1565 (NHCO), 745 and 695 cm$^{-1}$ (aryl); X-ray powder diffraction data: 15.22 w, 10.21 s, 7.69 m, 5.30 s, 5.06 w, 4.64 s (3), 4.41 s (2), 4.12 vs (1), and 3.77 w.

The mother liquor was evaporated to give the syrupy ribo derivative (Compound V); yield 22.5 g (87%), $[\alpha]_D^{23}$ +60° (c 1, chloroform); $\nu_{max}^{KBr}$ 3410 (NH), 1660, 1510 (NHCO), 755 and 700 cm$^{-1}$ (aryl).

The ribo Compound V and its arabino analogue had $R_f$ values of 0.64 and 0.59, respectively, in t.l.c. with 4:1 benzene-ethanol, and it was verified that each product was free from contamination by the other.

EXAMPLE 5

Conversion to methyl 3-acetamido-4-O-benzoyl-6-bromo-2,3,6-trideoxy-α-D-ribo-hexopyranoside (Compound VI)

To a solution of Compound V (16 g, 52 mmoles) in dry carbon tetrachloride (400 ml) were added N-bromosuccinimide (11 g, 61.8 mmoles) and barium carbonate (15 g). The mixture was boiled under reflux for 2 hours under normal room-illumination, during which time the mixture, originally colorless, became successively yellow, red, and, finally, faintly yellow. The solvent was removed in vacuo, and the residue was extracted with dichloromethane (200 ml); the clear extract was washed successively with 5% aqueous sodium hydrogen sulfite and aqueous sodium hydrogen carbonate, dried (magnesium sulfate), and evaporated. The resultant, crystalline residue was recrystallized from ethanol to give analytically pure Compound VI; yield 14 g (70%), m.p. 173° C, $[\alpha]_D^{22}$ +76.5° (c 1, chloroform); $\nu_{max}^{KBr}$ 3400 (NH), 1735 (ester C=O), 1675 and 1535 cm$^{-1}$ (NHCO); X-ray powder diffraction data: 14.36 m, 7.40 m (3), 6.91 w, 5.30 m (2), 5.02 w, 4.39 s (1), 3.34 w, 3.16 w, 3.11 w, and 2.89 vw.

Anal. Calc. for $C_{16}H_{20}BrNO_5$ (386.25): C, 49.76; H, 5.22; Br, 20.69; N, 3.63. Found C, 49.60; H, 5.52; Br, 20.41; N, 3.81.

EXAMPLE 6

Dehydrobromination to methyl 3-acetamido-4-O-benzoyl-2,3,6-trideoxy-α-D-erythro-hex-5-enopyranoside (Compound VII)

A mixture of Compound VI (5 g, 13 mmoles) and dry, technical-grade silver fluoride (5 g, 22.1 mmoles) in dry pyridine (90 ml) was stirred for 14 hours at 25° C, after which time, t.l.c. (2:3 benzene-acetone) showed that all of Compound VI had reacted. The dark solution was poured into ether (500 ml), and the resultant mixture was filtered. The filtrate was evaporated at 40° C, and then three 25-ml portions of toluene were added to and evaporated from the residue (to remove all of the pyridine). The resultant syrup was taken up in ether, and the suspension filtered through a small column (250 × 20 mm) of silica get to remove residual silver salts. The effluent was evaporated in vacuo to give the pure Compound VII as a syrup; yield 4 g (100%), $[\alpha]_D^{23}$ +55.2° (c, 1.4, chloroform); $\nu_{max}^{film}$ 3420–3290 (NH), 1725 (ester CO), 1660 (Amide I, C=C), 1600, 1585 (monosubstituted phenyl), and 1525 cm$^{-1}$ (Amide II).

Anal. Calc. for $C_{16}H_{19}NO_5$ (305.33): C, 62.94; H, 6.27; N, 4.56. Found: C, 62.52; H, 6.52; N, 4.21.

EXAMPLE 7

Debenzoylation to methyl 3-acetamido-2,3,6-trideoxy-α-D-erythro-hex-5-enopyranoside (Compound VIII)

To a solution of Compound VII (5 g, 16.4 mmoles) in absolute methanol (30 ml) was added M sodium methoxide (0.5 ml), and the mixture was kept for 12 hours at 25° C, at which point, t.l.c. (2:3 benzene-acetone) indicated that saponification was complete. The solution was passed through a small bed (250 × 20 mm) of silica gel in a column, and the effluent was evaporated in vacuo to give Compound VIII as a syrup, yield 3.2 g (97%); this was subjected, without delay, to the hydrogenation step of Example 8.

To secure an analytical sample free from methyl benzoate, the syrup was dissolved in water, the solution was washed twice with dichloromethane, and the aqueous solution was freeze-dried, giving pure Compound VIII; $[\alpha]_D^{22}$ +74.5° (c 1, water); $\nu_{max}^{film}$ 3500–3200 (OH, NH), 1655 (Amide I, C=C), and 1525 cm$^{-1}$ (Amide II).

EXAMPLE 8

Hydrogenation to methyl 3-acetamido-2,3,6-trideoxy-$\beta$-L-lyxo-hexopyranoside (Compound IX) (methyl N-acetyl-$\beta$-daunosaminide)

A solution of Compound VIII (1.5 g, 7.46 mmoles) in absolute methanol (50 ml) was hydrogenated in the presence of 10% palladium-on-barium sulfate (150 mg) at atmospheric pressure. After 30 minutes, the theoretical amount of hydrogen had been taken up, and t.l.c. (2:3 benzene-acetone) verified that the reaction was complete. The catalyst was filtered off, and the filtrate was evaporated in vacuo to give a crystalline, chromatographically homogeneous residue of Compound IX; yield 1.5 g (99%). For analytical purposes, a sample was recrystallized from ethyl acetate to give Compound IX as fine needles; m.p. 208°–210° C (sublimation), $[\alpha]_D^{22}$ −28° (c 1, water); $\nu_{max}^{KBr}$ 3440, 3280 (OH,NH), 1630 and 1530 cm$^{-1}$ (amide); X-ray powder diffraction data: 9.30 s (2,2), 7.37 m, 6.10 s (2,2), 5.08 vw, 4.68 m, 4.34 vs (1), 3.88 m (4), 3.71 s (3), 3.03 m, 2.87 m, 2.80 m, 2.54 m, 2.40 m, 2.28 m, 2.13 m, and 2.05 w.

Anal. Calc. for $C_9H_{17}NO_4$ (203.24): C, 53.19; H, 8.43; N, 6.89. Found: C, 53.15; H, 8.68; N, 6.81.

Compound IX could be clearly resolved by t.l.c. from its 5-epimer (the D-ribo analogue), but no trace of the 5-epimer was found in Compound IX or in the mother liquor from the crystallization.

EXAMPLE 9

Conversion to 3-Amino-2,3,6-trideoxy-L-lyxo-hexose hydrochloride (Compound X) (daunosamine hydrochloride)

A solution of Compound IX (300 mg, 1.48 mmoles) and barium hydroxide octahydrate (946 mg, 3 mmoles) in water (6 ml) was boiled for 12 hours under reflux, after which time, t.l.c. (2:3 benzene-acetone) revealed only a trace of the starting Compound IX ($R_f$ 0.36) accompanying the N-deacetylated product ($R_f$ 0.1). Solid carbon dioxide was added, and the resultant precipitate of barium carbonate was filtered off with suction. The filtrate was then lyophilized to give a solid that was dissolved in absolute ethanol and freed from traces of inorganic material by filtration. The filtrate was evaporated to dryness, and the residue dissolved in 0.5M hydrochloric acid (10 ml). The solution was heated for 3 hours at 100° C, decolorized with activated charcoal, and lyophilized to give a foam that readily crystallized on addition of acetone (4 ml). The crystals were filtered off in an inert atmosphere (nitrogen) and dried; yield 200 mg (84%) of daunosamine hydrochloride, m.p. 168°–170° C (dec.), $[\alpha]_D^{23}$ −65.4° (equil., c 1.3, water); X-ray powder diffraction data: 7.43 s (2), 7.02 w, 4.54 m (3), 4.18 vs (1), 3.73 m, 3.52 m, and 3.32 m.

The m.p. of the product was undepressed on admixture with an authentic sample of daunosamine hydrochloride, and an authentic sample of daunosamine hydrochloride showed the same X-ray diffraction lines as those recorded here. The two samples also showed identical i.r. spectra.

The embodiments of the invention in which an exclusive property or privilege is claimed are defined as follows:

1. A method for the synthesis of daunosamine hydrochloride from methyl $\alpha$-D-mannopyranoside, which comprises the steps of:
   a. benzylidenting said methyl $\alpha$-D-mannopyranoside to the 2,3:4,6-dibenzylidene acetal with $\alpha,\alpha$-dimethoxytoluene;
   b. converting said 2,3:4,6-dibenzylidene acetal into the 4,6-O-benzylidene-2-deoxy-3-keto compound with butyllithium;
   c. oximating the 3-keto group to the 3-oxime group with hydroxylamine;
   d. reducing said 3-oxime group to the 3-amino group with lithium aluminum hydride;
   e. acetylating said 3-amino group to the 3-acetamido group with acetic anhydride and recovering from the reaction mixture the 4,6-O-benzylidene-D-ribo-3-acetamido compound;
   f. converting said 4,6-O-benzylidene-D-ribo-3-acetamido compound into the 4-O-benzoyl-6-bromo-6-deoxy compound with N-bromosuccinimide;
   g. dehydrobrominating said 4-O-benzoyl-6-bromo compound to the 4-O-benzoyl-5,6-unsaturated compound with silver fluoride;
   h. debenzoylating said 4-O-benzoyl-5,6-unsaturated compound to the 4-hydroxy-5,6-unsaturated compound by catalytic transesterification with sodium methoxide;
   i. stereospecifically hydrogenating said 4-hydroxy-5,6-unsaturated compound in the presence of palladium-on-barium sulfate to give methyl N-acetyl-$\beta$-daunosaminide;
   j. N-deacylating said methyl N-acetyl-$\beta$-daunosaminide with aqueous barium hydroxide; and
   k. hydrolyzing the N-deacylated compound with aqueous hydrochloric acid to give daunosamine hydrochloride.

2. The method of claim 1, wherein said 4,6-O-benzylidene-D-ribo-3-acetamido compound is recovered from said reaction mixture in step (e) by mixing said reaction mixture with toluene to thereby precipitate the D-arabino diastereoisomer of said 4,6-O-benzylidene-D-ribo-3-acetamido compound, separating the precipitate from said reaction mixture, and evaporating the mother liquor of said reaction mixture.

3. The method of claim 2, wherein the mixing of said reaction mixture with toluene is carried out at a temperature of about 0° C.

4. The method of claim 1, wherein the conversion of said 2,3:4,6-dibenzylidene acetal into said 4,6-O-benzylidene-2-deoxy-3-keto compound in step (b) is carried out at a temperature below −30° C, and the molar ratio of said butyllithium to said 2,3:4,6-dibenzylidene acetal is at least 2:1.

5. The method of claim 4, wherein said temperature is within the range of from −30° to −55° C, and said molar ratio is 2.2:1.

* * * * *